(12) United States Patent
Brill (10) Patent No.: US 9,104,200 B2
(45) Date of Patent: Aug. 11, 2015

(54) METHOD FOR THE COLLISION-FREE POSITIONING OF A MICROMANIPULATOR TOOL

(75) Inventor: Norbert Brill, Gerlikon (CH)

(73) Assignee: MMI AG, Glattbrugg (CH)

( * ) Notice: Subject to any disclaimer, the term of this patent is extended or adjusted under 35 U.S.C. 154(b) by 418 days.

(21) Appl. No.: 13/641,264

(22) PCT Filed: Apr. 12, 2011

(86) PCT No.: PCT/EP2011/055695
§ 371 (c)(1),
(2), (4) Date: Nov. 21, 2012

(87) PCT Pub. No.: WO2011/141252
PCT Pub. Date: Nov. 17, 2011

(65) Prior Publication Data
US 2013/0090778 A1    Apr. 11, 2013

(30) Foreign Application Priority Data

Apr. 15, 2010 (EP) .................................. 10160009

(51) Int. Cl.
*G05D 3/00*   (2006.01)
*G01N 1/28*   (2006.01)
*G02B 21/32*  (2006.01)

(52) U.S. Cl.
CPC .................. *G05D 3/00* (2013.01); *G01N 1/286* (2013.01); *G02B 21/32* (2013.01)

(58) Field of Classification Search
CPC ........... G05D 3/00; G01N 1/286; G02B 21/32
USPC .................. 700/56, 57, 53, 60, 186, 193, 302
See application file for complete search history.

(56) References Cited

U.S. PATENT DOCUMENTS

| 4,907,158 | A |   | 3/1990 | Kettler et al. |
| 5,363,190 | A | * | 11/1994 | Inaba et al. .................... 356/337 |

(Continued)

FOREIGN PATENT DOCUMENTS

| DE | 102005053669 | 5/2007 |
| DE | 102007046267 | 4/2009 |

(Continued)

OTHER PUBLICATIONS

International Search Report for Corresponding PCT Application PCT/EP2011/055695 mailed May 8, 20092011.

*Primary Examiner* — Charles Kasenge
(74) *Attorney, Agent, or Firm* — Pabst Patent Group LLP (57) ABSTRACT

A method for the collision-free positioning of a micromanipulation tool relative to a sample carrier with the aid of a microscope, comprising the following steps: a) determining the focal position $Z_p$ of at least one point P on the surface of the sample carrier by focusing a microscope objective with a first numerical aperture $NA_1$ on the at least one point; b) positioning the micromanipulation tool on the optical axis of the microscope; c) determining the focal position $Z_M$ of the micromanipulation tool by focusing the microscope objective or a second microscope objective with a second numerical aperture $NA_2$ smaller than the first numerical aperture $NA_1$ onto the tip of the micromanipulation tool; d) calculating the lowering distance $Z_A(P)$ taking into account a predetermined tolerance profile $\Delta Z$ by the following equation: $Z_A(P)=Z_M-Z_p-\Delta Z$ where $\Delta Z=\Delta Z_M+\Delta Z_p$, wherein $\Delta Z_M$ and/or $\Delta Z_p$ is a predetermined tolerance in the determination of the position of the manipulation tool and sample carrier, respectively; and e) positioning the micromanipulation tool at the point P by lowering by the lowering distance $Z_A(P)$.

10 Claims, 4 Drawing Sheets

(56) References Cited

U.S. PATENT DOCUMENTS

| | | | |
|---|---|---|---|
| 5,410,259 A | 4/1995 | Fujihara et al. | |
| 5,886,684 A | 3/1999 | Miura et al. | |
| 6,164,514 A * | 12/2000 | Miller | 228/1.1 |
| 6,382,494 B1 * | 5/2002 | Miller | 228/1.1 |
| 6,411,433 B1 * | 6/2002 | Miyoshi | 359/396 |
| 6,711,283 B1 | 3/2004 | Soenksen | |
| 6,986,739 B2 * | 1/2006 | Warren et al. | 600/159 |
| 2003/0021017 A1 * | 1/2003 | Eijsackers et al. | 359/368 |
| 2004/0172014 A1 | 9/2004 | Maass | |
| 2005/0174085 A1 * | 8/2005 | Yuri | 318/640 |
| 2007/0047073 A1 | 3/2007 | Zimmer et al. | |
| 2007/0177258 A1 * | 8/2007 | Eijsackers et al. | 359/393 |
| 2009/0078885 A1 | 3/2009 | Kilper | |
| 2009/0291502 A1 | 11/2009 | Tateyama | |
| 2009/0303321 A1 | 12/2009 | Olson et al. | |

FOREIGN PATENT DOCUMENTS

| | | |
|---|---|---|
| EP | 0292899 | 11/1998 |
| JP | 63-011614 | 1/1988 |
| JP | 06-167656 | 11/1992 |
| JP | 07-168101 | 12/1993 |
| JP | 09-304703 | 11/1997 |
| JP | 10-068888 | 3/1998 |
| JP | 2005-326341 | 5/2004 |
| JP | 2005-258413 | 9/2005 |
| JP | 2005258413 | 9/2005 |
| JP | 2006-106192 | 4/2006 |
| JP | 2007-525689 | 9/2007 |
| JP | 2009-202269 | 2/2009 |

* cited by examiner

METHOD FOR THE COLLISION-FREE POSITIONING OF A MICROMANIPULATOR TOOL

CROSS REFERENCE TO RELATED APPLICATIONS

This application is a national phase filing under 35 U.S.C. §371 of PCT/EP2011/055695 filed under the Patent Cooperation Treaty on Apr. 12, 2011, which claims priority to and benefit of foreign application EP 10160009.6, filed on Apr. 15, 2010, the contents of each being hereby incorporated by reference in their entirety.

The present invention relates to a method for the collision-free positioning of a micromanipulation tool, in particular a tool for microinjection, individual cell removal, microdissection and the like.

PRIOR ART

The molecular analysis of pure enriched cell cultures or even individual cells is an important prerequisite of medical genomics and proteomics, and could become extremely important in the future for a medical profiling of patients. Hitherto this objective could be achieved only with difficulty and took a not inconsiderable amount of time on account of mechanical and also process technology restrictions in the cell manipulation (e.g. the collection of cells or the microinjection). In particular the isolation of individual as well as unusual cells from minute samples necessary for the genotype and phenotype characterization proved to be very difficult, since individual cells had to be detected under a microscope by research staff and the detected cells then had to be manipulated manually with the aid of capillaries.

In order to allow an automation of the cell isolation, in other words in particular the collection of individual cells, an exact determination of the position of the capillary tip, that is the manipulated tip, in the X-, Y- and Z-direction relative to the sample carrier of a microscope would be necessary taking into account all tolerances, which are due to the objective lens and the not exactly planar and horizontal surface of the sample carrier. Hitherto it was not possible however to determine in an automated manner with a sufficiently small tolerance the actual position of the manipulator tip in the Z-direction without additional measurement means. Accordingly the collection of individual cells of particles was possible only manually or in a semi-automatic way. Although some approaches to the automation of this procedure are known, which however in these previously known methods did not take account of the imaging tolerances of the objective lens, damage to the manipulated tip still occurred.

With manual calibration methods on the other hand the handling tools are often not sufficiently accurate, with the result that only very skilled users can master these systems.

In EP 0 292 899 B1, for example, after inserting the vessel with the cells to be collected the microscope is firstly focused on the capillary tip, which is positioned in the centre of the field of view of the microscope. Thereupon the microscope is focused on the plane of the cells on the floor of the vessel and the capillary is lowered by hand until it penetrates the sample, penetration being established by a visual check. The position in the X-Y plane as well as the extent of movement in the Z-direction during the lowering procedure are detected and stored in a control computer, which in the following procedures uses these data for the automatic broaching of further cell positions selected in the coordinate system by computer. A disadvantage with the methods described here is that the distance to the slide (in other words the position at which the capillary can be damaged) is not determined, but simply the Z-coordinate of the surface of an arbitrarily selected cell from the biological sample. Tolerances are also not taken into account. It therefore cannot be excluded that the capillary tip and the slide collide and the capillary is thereby damaged. In addition the fine adjustment is carried out in this case by a test injection into the arbitrarily selected cell. Since in this case cells that are indeed derived from the same cell culture but have different external geometries deposit on the slide, this type of calibration to determine the position is very inaccurate.

In DE 10 2005 053 669 B4 a sample manipulation device is described, in which the actual position of the manipulator tip is determined with the aid of a position measurement unit designed as a microscope, while the desired position on or in the sample is observed with an observation unit likewise designed as a microscope and arranged on the other side of the sample stage. By comparing the data from the observation unit and position measurement unit the control device can adjust the manipulator tip to the desired position. The disadvantage with this sample manipulation device is that the position measurement objective lens has a depth of focus of the order of magnitude of the manipulator tip, and therefore the determination of the Z-direction is correspondingly inaccurate, with an error that corresponds roughly to the diameter of the capillary itself. This error is however not taken into account for the positioning. Also, the position of the slide in the Z-direction is not determined, so that given the possible deviation of the real position from the calculated position on account of the error of the position measurement objective, collisions between the slide and manipulator tip can occur.

Finally, in DE 10 2007 046 267 A1 the sampling tool, for example a capillary, is accommodated by a receiving element on a tool head, which determines the spatial position of the cell object in a sample vessel by means of an image recording unit and an image evaluation unit, and the sampling tool is advanced by means of a control and storage unit and a drive mechanism first of all to a calibration position and then to a position above the cell object. Next the image recording unit and the image evaluation unit also detect the spatial position of the sampling tool above the cell object and determine a deviation from the desired position. The control and storage unit then corrects the position of the sampling tool by means of the drive mechanism. Also with this sample manipulation device the capillary tip has to be driven to the calibration position in the field of view of the microscope, which at large magnifications can however only be performed manually. When the sampling tool is lowered the tolerances, which are determined for example by the depth of focus of the microscope objective, are furthermore not taken into account, which can lead to an incorrect calculation of the distance to be maintained and thus to collisions.

Finally, in none of the aforementioned documents is the profile of the slide determined, that is the variation of the Z-position of its surface as a function of the position in the X-Y plane, so that after advancing to a new X-Y position the distance is possibly again not correctly calculated on account of the change of the Z-coordinate of the slide surface, and the capillary tip can collide with the slide. Although according to DE 10 2007 046 267 A1 an additional sensor or a spring mounting for the manipulation tool can be provided for the case of such a collision, this however does not reliably exclude damage and furthermore leads to defective sampling and therefore to lost time.

Also in the case of obliquely, i.e. not exactly horizontally inserted slides, which is a situation frequently encountered in practice but seldom realised by technical staff, errors in the position of the capillary occur. The capillary could be damaged already when moving to the start position, especially if the start position is only a few µm from the slide surface. In practice the Z-positions on an oblique slide in the region of interest differ by up to 30 µm, and if furthermore the microscope insert for the slide is contaminated by dust or the like, the Z-positions can differ by more than 100 µm. When using glass Petri dishes the error can finally amount to a multiple of this value. If however a contact calibration with step widths of <1 µm is used, then for safety reasons much greater distances of the start position from the slide (>100 µm) would have to be maintained, which in practice leads to significant disadvantages since at step widths <1 µm a contact calibration would then take too much time.

DESCRIPTION OF THE INVENTION

The object of the present invention is accordingly to provide a method for the collision-free positioning of a micromanipulation tool relative to a sample carrier, which permits an accurate and damage-free positioning of the manipulation tool over the whole sample surface in a completely automated manner. This object is achieved by a method having the features of claim 1. Preferred advantageous configurations of the invention are defined in the dependent claims.

The method according to the invention for the collision-free positioning of a micromanipulation tool relative to a sample carrier with the aid of a microscope comprises the following steps:

a) determining the focal position 4 of at least one point P on the surface of the sample carrier by focusing a first microscope objective with a first numerical aperture $NA_1$ on the at least one point; b) positioning the micromanipulation tool on the optical axis of the microscope; c) determining the focal position $Z_M$ of the micromanipulation tool by focusing the aforementioned microscope objective or a second microscope objective with a second numerical aperture $NA_2$ smaller than the first numerical aperture $NA_1$ onto the tip of the micromanipulation tool; d) calculating the lowering distance $Z_A(P)$ taking into account a predetermined tolerance profile $\Delta Z$ by the following equation:

$$Z_A(P) = Z_M - Z_P - \Delta Z$$

where $$\Delta Z = \Delta Z_M + \Delta Z_P$$

wherein $\Delta Z_M$ and $\Delta Z_P$ is a predetermined tolerance in the determination of the position of the manipulation tool and of the sample carrier, respectively; e) positioning the micromanipulation tool at the point P by lowering by the lowering distance $Z_A(P)$.

The terms tolerance and tolerance profile are understood by the person skilled in the art to mean in this connection an inaccuracy in the position determination associated with one of the (individual) optical components or with the overall optical system, which in cell microscopy is normally specified in units of µm ($10^{-6}$ m). Thanks to the method according to the invention the manipulation tool can thus be moved without collision over the sample carrier so long as the tool is outside the tolerance profile of the sample carrier. The manipulation tool can be detected by an objective lens with a small numerical aperture at a distance of for example 1 to 2 mm from the sample carrier, this distance being sufficiently accurately predetermined by the geometry of the microscope and manipulator. A collision can thus be reliably avoided. Overall the function, efficiency, reliability and, last but not least, the user friendliness of a micromanipulation device can thus be improved by the method according to the invention. In routine use the system can operate fully automatically, though the method here is not restricted to a completely automatic sequence and execution of the individual process steps. It is still possible to carry out the determination of the focal positions as well as the positioning in the X and Y direction and/or the lowering (raising) in the Z direction manually. Equally, regardless of the type of operation that is chosen, the method allows the micromanipulation tool to be positioned with a very high positioning accuracy of a few micrometers and to thereby avoid a collision between the sample carrier and tool at the same time. In particular, the manipulation tool can be moved above the sample carrier within a distance smaller than the sample diameter and/or the diameter of the tool itself. Finally, the time that is otherwise required for calibration is greatly reduced, since a start value for measurements is already predefined for the method by determining the focal position of the sample carrier.

The focal position is in this connection the Z-coordinate of the position of the relevant point, measured on or in the vicinity of the optical axis, at which a sharp image of the point observed through the microscope objective of the measurement is obtained, wherein the imaging sharpness can be determined automatically by a focusing system with image sensors or manually by observing the image of a video camera which shows the point to be focused.

In the positioning of the micromanipulation tool on the optical axis of the microscope a predetermined distance should be maintained, which usually is 1 to 2 mm from the sample carrier.

Preferably, before carrying out step e) of lowering the manipulation tool, steps c) and d) are repeated with a respective further, i-th microscope objective (i>1 or i>2) with a respectively increasing numerical aperture ($NA_i > NA_{i-1}$). This means that the position of the manipulation tool is first determined in step c) with the first microscope objective (numerical aperture $NA_1$), or with the second microscope objective, whose numerical aperture $NA_2$ is smaller than that of the first microscope objective for determining the focal position of the sample carrier, and in step d) the lowering distance is calculated taking into account a predetermined tolerance profile, but then a further objective with a higher numerical aperture and correspondingly smaller predetermined tolerance than the preceding objective can be used to improve the accuracy of determination of the position of the manipulation tool, and in this way the tolerance profile, which represents the safety margin for the positioning of the manipulation tool, can be made smaller. This procedure can be repeated iteratively, whereby high precisions in the micrometer range can be achieved.

Although according to the invention the tolerances $\Delta Z_M$ and $\Delta Z_P$ of the manipulation tool and of the sample carrier can be arbitrarily predetermined, in a particularly preferred embodiment of the invention it is envisaged that the tolerance $\Delta Z_M$ of the manipulation tool and/or the tolerance $\Delta Z_P$ of the sample carrier is given by the depth of focus $d_{tief,i}$ of the respective i-th objective used for its position determination, according to the following equation:

$$\Delta Z_{M,P} = d_{tief,i} = \frac{\lambda \cdot n}{NA_i^2} + \frac{n}{M_i \cdot NA_i} \cdot e$$

$$i = 1, 2, \ldots$$

where λ is the wavelength of the observation light, n is the refractive index of the medium between the microscope objective and sample carrier, $M_i$ is the magnification of the i-th objective, and e is the resolving power of a video camera used for the observation.

The wavelength of the observation light is in this connection preferably a wavelength of 550 nm, which provides accurate results also when using white light (i.e. a continuum of wavelengths in the range from approximately 400 to 700 ma). The refractive index depends on the employed medium between the microscope objective and the sample carrier and is as a general rule the refractive index of air (n=1), although the use of immersion optics is also possible, in which the medium between the microscope objective and sample carrier is an immersion oil (n=1.515) or water (n=1.33). The video camera preferably has a standard resolving power of e=10 μm, although obviously finer or coarser resolving video cameras can be used. By using the depth of focus as a parameter in the determination of the tolerance profile, the possible deviation, in other words the measurement error, in the determination of the position of the sample carrier surface and manipulation tool when lowering the tool can now be taken into account in a reproducible and reliable manner, and therefore collisions with the sample carrier surface can be safely avoided.

In a further preferred embodiment, before step e), steps a) to d) are carried out for a plurality of predetermined points $P_j$ (j=1, 2, . . . ) on the surface of the sample carrier, the corresponding lowering distance $Z_A(P_j)$ for each point $P_j$ is stored in a database, and step e) is carried out for each point $P_j$ taking into account the stored lowering distance $Z_A(P_j)$. In this way, with a suitable choice of the plurality of predetermined points, even with uneven bases of the sample carriers, the sample carrier surface can be scanned with an objective of large numerical aperture before the sample manipulation and the corresponding lowering distance including the tolerance profile can be stored for each point $P_j$ as a function of its X and Y coordinates, and can be accessed during a later selection of an arbitrary point from the plurality of points for the sample manipulation. Alternatively it is possible to store, instead of the lowering distance $Z_A(P_1)$, the focal position of the point $P_j$, its X and Y coordinates, and also data on the objective, including details of its numerical aperture and magnification. By establishing such a topography of the sample carrier surface sample carriers with uneven surfaces, such as for example Petri dishes and the like, can also be used in the micromanipulation and can also be handled completely automatically.

Preferably, before step e), steps a) to c) are carried out for three points $P_1$, $P_2$, $P_3$ on the surface of the sample carrier not lying on a straight line, an equation of a plane E(P) is calculated from their determined focal position $Z_{P1}$, $Z_{P2}$, $Z_{P3}$, and in step d) the lowering distance $Z_A(P_1)$ for an arbitrary point $P_j$ on the surface of the sample carrier is calculated by $Z_A(P_j)=Z_M-E(P_j)-\Delta Z$.

This is especially advantageous if an otherwise plane sample carrier, such as for example a slide (slide), does not lie exactly perpendicular to the optical axis on the microscope stage, which is a relatively common source of error. This means that the plane of the slide runs out from the focal plane as soon as the microscope stage is moved to another position. The distance between the manipulation tool and slide plane would therefore also change. Due to this embodiment of the method the microscope control is able to compensate this effect and to maintain the focus on the sample carrier and, thus, the distance between the sample carrier and manipulation tool independently of the X-Y position on the sample carrier.

Preferably in step c) the position of the tip of the manipulation tool is determined as the focal position $Z_M$. In this way it is ensured that the operative part of the manipulation tool coming closest to the sample carrier is calibrated in its position, and thus contact and possible damage by collision of the tool with the sample carrier is avoided.

In a further particularly preferred embodiment a rotation angle and a tilt angle of the manipulation tool are compensated in step c) by carrying out the following steps:

c1) determining the focal position $Z_{Q1}$ of a first point $Q_1$ on the tip of the manipulation tool by focusing on the point $Q_1$ c2) rotating the manipulation tool about its axis and readjusting the microscope objective in order to focus the point $Q_1$ until the focal position $Z_{Q1}$ of the point $Q_1$ and a focal position 42 of a second point $Q_2$ on the tip of the manipulation tool are identical, c3) determining the focal position $Z_{Q3}$ of a third point $Q_3$ on the tip of the manipulation tool by focusing on the point $Q_3$, c4) tilting the manipulation tool about an axis parallel to the plane of the sample carrier and readjusting the microscope objective in order to focus the point Q3 until the focal positions $Z_{Q1}$, $Z_{Q2}$ and $Z_{Q3}$ are identical, c5) fixing the focal position of the manipulation tool $Z_A=Z_{Q1}$.

By compensating the tilt angle and the rotation angle of the manipulation tool it is possible to achieve extremely high accuracies in the calibration of the position of the manipulation tool relative to the sample carrier, since the shape of the end surface of the manipulation tool interacting with the sample is also taken into account. This is important especially with extruded capillaries or those capillaries whose tip is ground or cut at an angle. It is thereby actually ensured that the opening of the capillary and the active side of the manipulation tool are positioned at a minimal and uniform distance from the sample, and in the case of the capillary an optimal aspiration and flushing action can thereby be achieved on account of the very small distance. The rotation of the manipulation tool about its axis is preferably carried out in steps of up to a maximum ±5°. This is perfectly acceptable however since the capillary is already coarsely preadjusted beforehand with the aid of an alignment mark. The same also applies to the angle of inclination of the capillary, which for example is tilted by an electric drive preferably in small steps of up to at most ±2°, and here, too, the angle of inclination was coarsely preadjusted beforehand with the aid of the angle mark.

According to a further embodiment, in step a) in addition the focal position $Z_{cap}$ of a point R on the surface of a receiving vessel can be determined by focusing the first microscope objective on the point R. In this way it is possible to carry out a calibration also with respect to a receiving vessel, in which cell material taken from the sample carrier is deposited, for example. Since when depositing in a receiving vessel such as for example a cap or a tube, the same deposition position is always approached, in contrast to a grid on a slide, only a focal point in the receiving vessel has to be determined here, which speeds up the method.

Preferably the point or points on the surface of the sample carrier and/or on the surface of the receiving vessel are approached by displacing the vessel with the aid of a positioning table, such as for example a microscope stage. Here, the positioning table operates in the X-Y plane, so that a decoupling of focusing and horizontal positioning is achieved.

In a further embodiment it is also conceivable to carry out the determination of the focal position with the aid of an optical distance measurement system. In this way the focusing can also be carried out in a fully automatic manner with an accuracy in the sub-micrometer range.

Capillaries made of glass or metal, pipettes, needles or adhesive caps may be mentioned as examples of implementation of micromanipulation tools, wherein the manipulation tool can also consist of several manipulation tips in combination, for example an arrangement of a number n of capillaries or a combination of capillary, needle and adhesive cap. Finally, it is also conceivable for the micromanipulation tool to be a combination of manipulation tips with other optical micromanipulation tools, such as for example a capillary and micro-dissector, capillary and tweezers, capillary, micro-dissector and tweezers, or adhesive cap and tweezers.

BRIEF DESCRIPTION OF THE DRAWINGS

The invention is described in more detail hereinafter with the aid of embodiments examples, which are schematically illustrated with the aid of the following figures.

WAYS OF IMPLEMENTING THE INVENTION

By way of introduction, first the automated isolation of arbitrary individual or unusual cells is described, which is carried out in three steps: cell recognition, cell collection and cell release, before going on to describe preferred embodiment examples of the present invention with reference to the drawings.

The inventors have for this purpose developed a system that is based on an inverse microscope (inverted microscope), a cell recognition unit, an automated capillary adjustment, an automated pump and a sliding table. The collection and release are controlled with the aid of a high-precision pump (described in detail hereinafter), which enables process sequences to be specified that employ nanoliter volumes of a pump medium for the cell separation process, and thus provide the basis for a molecular analysis of the cell material to be performed at the end of the process in just 1 microliter of medium.

The (non-adhering) cells thus do not experience any kind of mechanical stress: the cell collection takes place simply on account of the liquid flow surrounding the cell. Under optimal conditions even partially adhering cells can be collected in this way. There is no contact between the cells and the capillary used for the collection. The capillary diameter can be significantly larger than that of the cell. For example, cells of 6 μm diameter can be collected efficiently with a capillary of 40 μm diameter.

The cells can be released on various target carriers (deposits). Here, so-called "grid deposits" are either grid-like point deposits (such as for example AmpliGrid®) or small vessels arranged like a grid (such as the IBIDI sample pocket slides). Individual point deposits can consist of a transparent cover, a PCR test tube or a microfluidic device. Whatever the type of target carrier, its size should in general not exceed the size of standard slides, so that these can be used in the multiple-slide holder on the sliding table. The holder would have to be adapted for larger target carriers, such as for example well plates.

The collection and release of the cells can take place in various ways, ranging from the manual to a fully automated mode of operation with cell recognition. However, even with the manual mode of operation it is not necessary to operate any components of the system (microscope, pump, capillary) by hand: all operating procedures are started by the user from a PC.

Figure 1A:
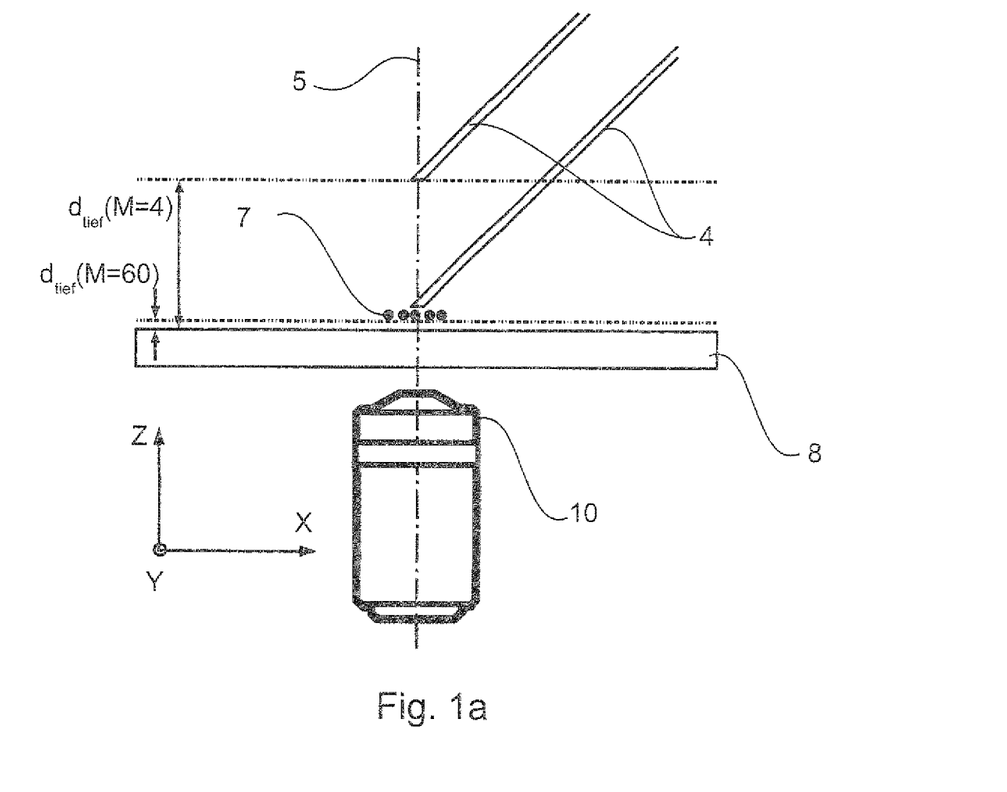
FIG. 1a) is an enlarged schematic section of a micromanipulation device during calibration of a micromanipulation tool, and FIG. 1b) is a schematic representation of the inclination of the sample carrier.
Figure 2:
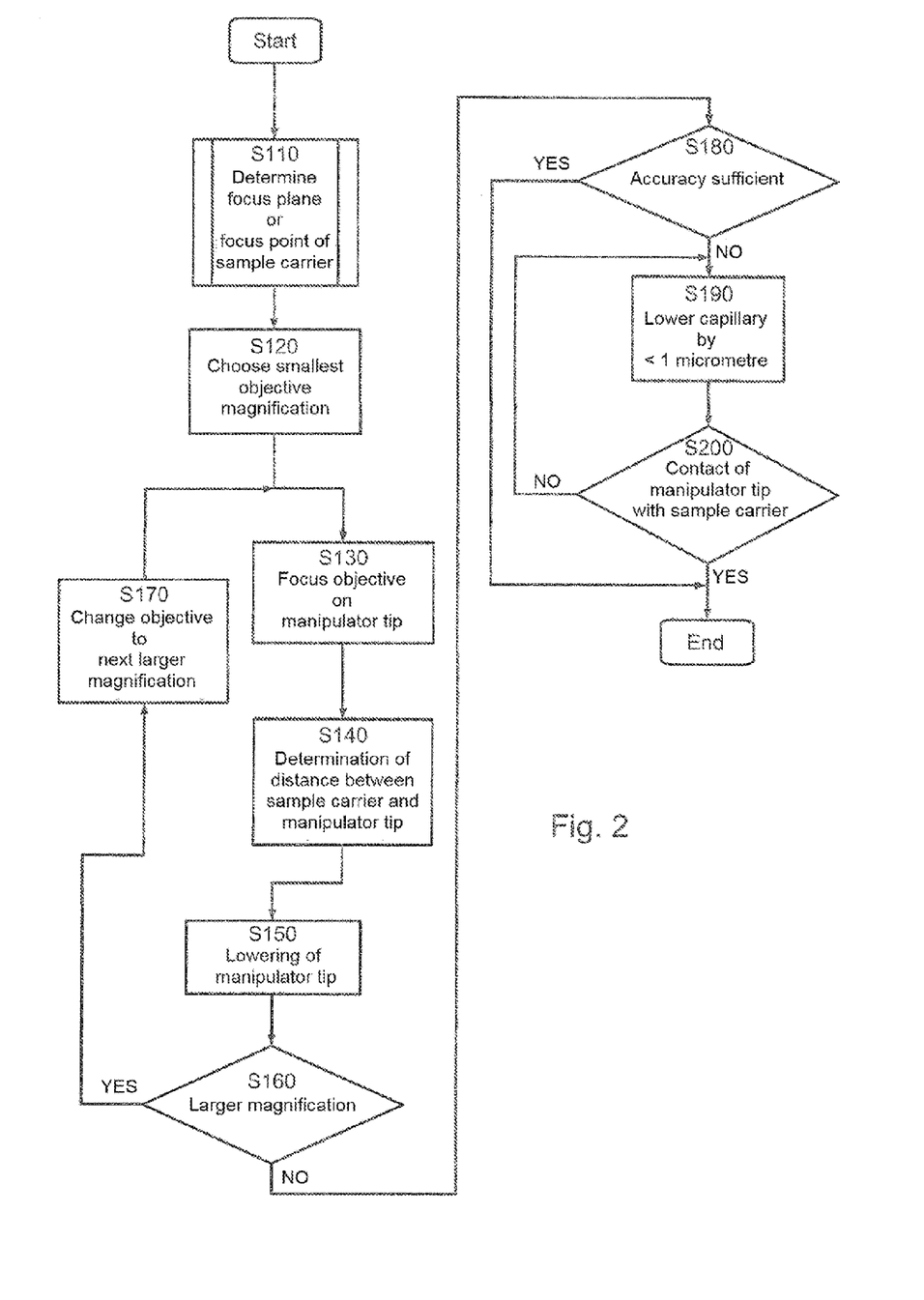
FIG. 2 is a flow diagram to illustrate the method sequence according to the invention for calibrating the micromanipulation tool.

A slide 8 is schematically illustrated in FIG. 1a), on which sample material 7, for example individual cells, are supported. The microscope slide 8 can be positioned in the X-Y direction on a microscope stage (not shown). The positioning in the Z-direction, that is the focusing, is carried out by adjusting an objective 10 along the optical axis 5. In the present exemplary embodiment a capillary 4 is shown as micromanipulation tool. In FIG. 2 on the other hand a flow diagram is shown, with the aid of which the method according to the invention, together with FIG. 1a) and b), is now described.

Figure 1B:
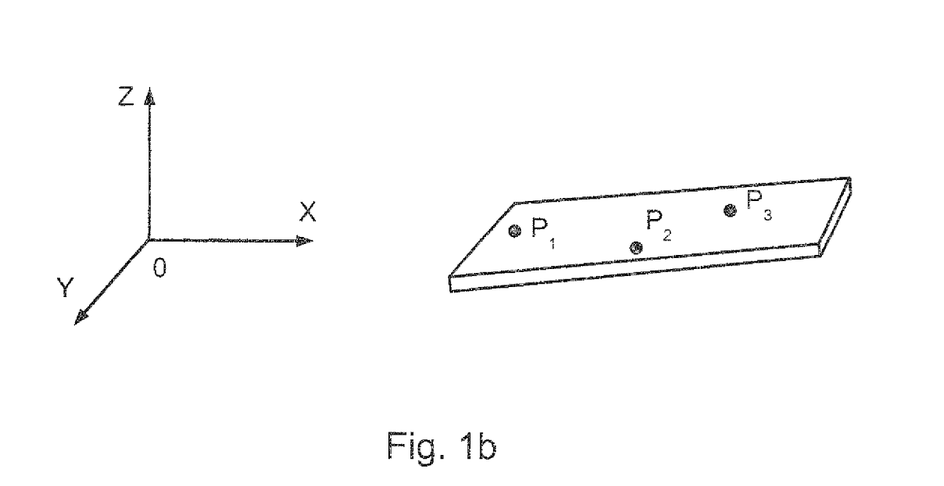

As is evident from FIGS. 1a) and b), in the present exemplary embodiment the sample carrier 8, a conventional slide made of glass, is disposed not exactly perpendicular to the optical axis 5 on the microscope stage (not shown), but is inclined at a small angle. This means that the slide plane runs out from the focusing plane as soon as the microscope stage is moved to another position. The distance between the tip of the capillary and the slide plane would thereby also change. In order to prevent this, the tilt angle of the slide 8 must be known, and the two effects can then be compensated.

In step S110 (FIG. 2), at the start of determining the focusing plane the objective 10 to be used for this purpose is first chosen, with a stronger magnification leading to a more accurate determination of the angle of inclination on account of smaller tolerance profiles. A comparison of the tolerance profiles of objectives of different magnifications and numerical apertures is shown in Table 1.

TABLE 1

Tolerance profiles of various microscope objectives
($\lambda = 550$ nm, n = 1, e = 10 μm)

| Magnification of the objective (M) | Numerical aperture (NA) | Tolerance profile $d_{tief}$ [μm] |
|---|---|---|
| 4 | 0.13 | 103.6 |
| 10 | 0.3 | 18.8 |
| 20 | 0.45 | 7.6 |
| 40 | 0.6 | 3.8 |
| 60 | 0.7 | 2.8 |
| 100 | 0.95 | 1.4 |

In the present case, an objective with $M_1=60$ and $NA_1=0,7$ is chosen, i.e. one with a large numerical aperture. Three points $P_1$, $P_2$ and $P_3$ on the slide 8, not all of which lie on a common line and thus define the plane of the slide 8, are now approached in succession. The objective 10 is first moved over the position of a point $P_1$ by means of the adjustment drive (microscope stage) and focused on the point $P_1$. The X-Y coordinates at well as the coordinate $Z_{P1}$ of the focal position of the point $P_1$ are determined and stored in the microscope control. The microscope stage then moves to the second position, at which the objective is located over the point $P_2$. The objective 10 is focused on the point $P_2$ and the X-Y coordinates as well as the Z-coordinate (focal position $Z_{P2}$) are stored. Finally the microscope stage is moved to the X-Y position at which the point $P_3$ is located on the optical axis 5. The X, Y coordinates and the focal position $Z_{P3}$ are stored. The control can now establish an equation of a plane E(P) with the aid of the X, Y and Z-coordinates of the three stored points on the slide surface, and can determine the angle of inclination of the slide with respect to the horizontal (step S110).

In the next step S120 the smallest available objective magnification (smallest numerical aperture) is now chosen so as to determine the position of the manipulation tool 4. In the following example an objective 10 is chosen for this purpose, with a numerical aperture $NA_2$ of 0,13 and a magnification $M_2=4$. The micromanipulation tool 4, in the present case a capillary, is moved with its tip onto the optical axis 5 and positioned at a distance of 1 to 2 mm from the slide 8. With the aid of the objective 10 with the smallest objective magnification the focal position $Z_M$ of the capillary tip is now determined by focusing on the tip (S130). Using the above data the distance between the focal plane of the slide and manipulation tip can be determined for each point in the X-Y plane and is $Z_M-E(P)$ (S140). However, this distance still does not take into account the tolerances inherent in the determination of the position of the capillary 4 as well as of the slide 8; these must be taken into account in order to prevent too deep a lowering of the capillary tip 4. In the following case the tolerances of the position determination are predetermined by the objective parameters and can be calculated as follows. Here, the region of sharp focus, termed the depth of focus, is the extension of the region in the object space of an imaging optical system that is imaged with sufficient sharpness onto the image plane.

$$\Delta Z_{M,P} = d_{tief,i} = \frac{\lambda \cdot n}{NA_i^2} = \frac{n}{M_i \cdot NA_i} \cdot e$$

$$i = 1, 2, \ldots$$

From this equation it follows that in order to reduce the depth of focus and thus increase the precision in the position determination, on the one hand objectives with a larger numerical aperture or magnification can be used, or alternatively light of shorter wavelength can be employed. Since in routine operations it is for practical reasons not desirable to change the wavelength of the micromanipulation system, in the present case the magnification or the numerical aperture of the objective is changed in order to improve the positioning accuracy.

In order therefore to prevent a collision of the capillary 4 with the slide 8, a tolerance profile $\Delta Z = \Delta Z_M + \Delta Z_p$ is subtracted from the distance between the capillary tip and slide, into which are incorporated the depth of focus of the two objectives previously used for the position determination, once for the slide and the other time for the capillary tip. The lowering distance $Z_A(P)$ is thus determined as follows depending on the focal positions of the capillary tip and slide taking into account the tolerances specified by the depths of focus:

$$Z_A(P) = Z_M - E(P) - \Delta Z$$

$$= Z_M - E(P) - d_{tief,1} - d_{tief,2} =$$

-continued $$= Z_M - E(P) - \left(\frac{\lambda \cdot n}{NA_1^2} + \frac{\lambda \cdot n}{NA_2^2} + \frac{n}{M_1 \cdot NA_1} \cdot e + \frac{n}{M_2 + NA_2} \cdot e\right)$$

Then the probe is lowered by the amount $Z_A(P)$ (S150). It only remains to be determined whether the present microscope magnification and thus the accuracy of the tolerance determination is sufficient or not for the application (S160). If a larger working magnification is required, then an objective with larger numerical aperture can be used (S170) and the determination of the capillary tip can be repeated with greater precision (S130-S150). The value for the depth of focus of the objective, which was used for the now employed further (i-th) position determination of the capillary tip, is then appropriately substituted in the above equation. The value for the depth of focus that was used for the position determination of the slide remains unchanged.

If the accuracy now turns out to be sufficient (S180), the calibration can be terminated. However, there may be situations in which an even more accurate positioning is required, but an objective with a larger numerical aperture is no longer available. In such a case it is possible to lower the capillary tip in steps of less than 1 μm (S190) until the tip gently touches the surface of the slide (S200). As a result of this contact the capillary is bent (but due to its elasticity does not break) and therefore its position in the X-Y plane also changes, which can be detected under the microscope. In this way a maximum lowering can be defined, which must not be exceeded for this point. After this determination of the contact point between the capillary and the slide the accuracy of the capillary tip position relative to the slide now no longer depends on the magnitude of the tolerance profile, but on the accuracy of the Z-axis of the manipulator, so that a position accuracy of less than 1 μm is achieved.

Tests have shown that it is sufficient to start the calibration procedure with the smallest magnification and then to switch to the objective with the largest magnification. In this way the time needed for the calibration is significantly reduced. For small operating magnifications (up to a maximum of 20×), when using an objective with a large operating distance, the calibration can be carried out directly with the working objective. In this case the position of the slide as well as that of the capillary tip is therefore determined with an objective, and a value of twice the depth of focus of the objective is taken as tolerance profile. No change of objective is thus required.

Figure 3:
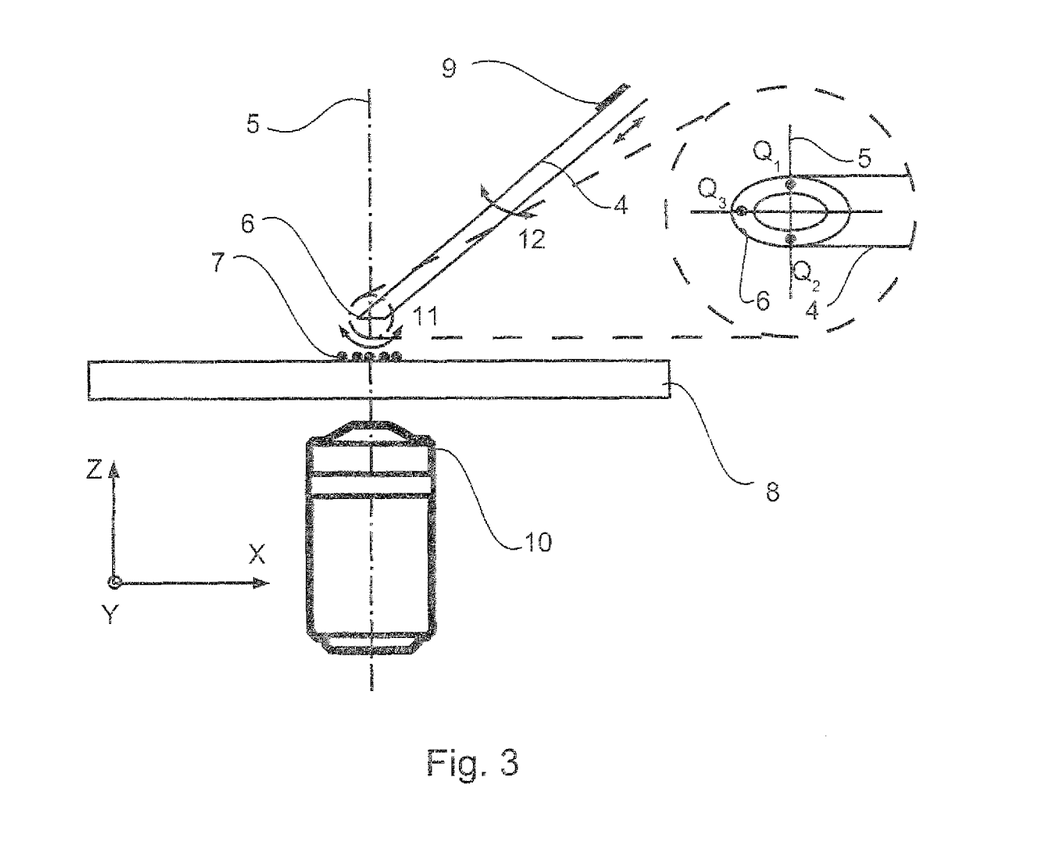
FIG. 3 is a schematic representation of the correction of the tilt angle and of the axial rotation angle of the manipulation tool.
Figure 4:
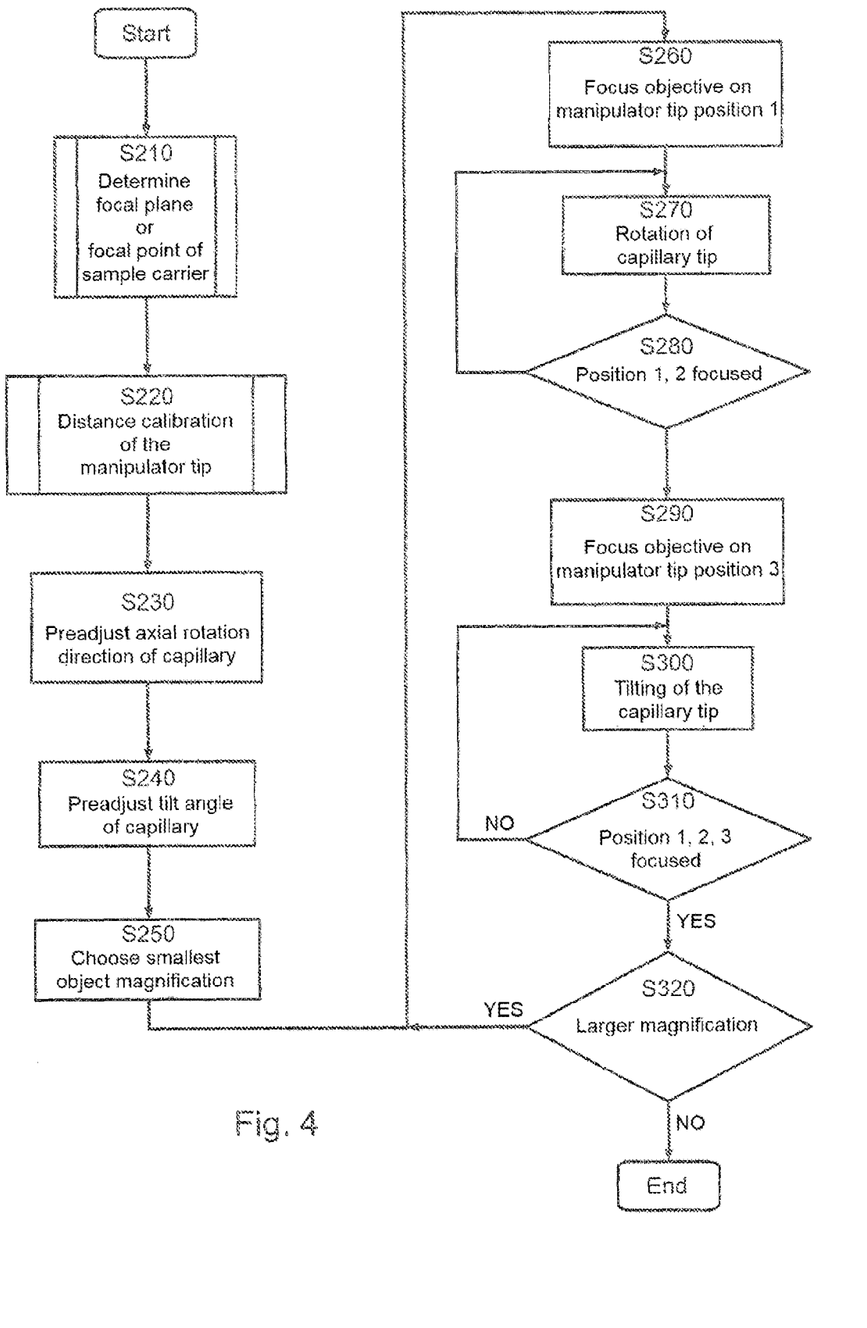
FIG. 4 is a flow diagram to illustrate the method for correcting the tilt angle and the rotation angle.

In a further embodiment, which is illustrated with the aid of FIG. 3, the tilt angle 11 and the rotation 12 of the capillary 4 are compensated before the calibration. Such a tilting and rotation means that the cell culture to be collected and the opening of the capillary 4 facing the slide 8 do not lie in a plane parallel to the slide and accordingly can result in a non-uniform aspiration action or rinsing action of the capillary 4, since one side of the capillary tip is further from the slide 8 and the cell material 7 than the other side. After the angle of inclination of the slide 8 has been calculated as described above (S210) and the capillary has been lowered (S220), the capillary tip is initially moved to the optical axis 5 and the axial rotation 12 of the capillary 4 is pre-adjusted with a direction marker 9 when the capillary is inserted into the capillary holder (S230). Also, the tilt angle 11 is coarsely pre-adjusted with the aid of the marker 9 (S240). As previously, the objective 10 with the lowest magnification is selected and the tip of the capillary 4 is moved to the optical axis 5 (S250). The distance between the slide 8 and capillary tip is ca. 1 to 2 mm. The objective 10 is then focused on a point Q1 on the capillary tip and its X, Y and Z coordinates are stored (S260).

The capillary 4 is rotated with an electric drive in small steps about its axis (S270), until both the point Q1 and a second point Q2 are focused on the capillary tip (S280). The maximum rotation here is ±5°. The new Z coordinate of the objective 10 is determined by refocusing on Q1. If the points Q1 and Q2 cannot be simultaneously imaged in sharp focus, then the capillary 4 is rotated again in small steps until the points Q1 and Q2 are finally jointly focused.

A further point Q3 on the capillary tip is then moved to the optical axis by operating the micromanipulator, and focused with the objective 10 (S290). The X, Y and Z coordinates of the point Q3 are stored.

The tilt angle 11 of the capillary 4 is now tilted in small steps, by a maximum of ±2° (S300), by means of an electric drive. The Z coordinate of the objective is determined by refocusing on the point Q1. If the points Q1, Q2 and Q3 cannot be simultaneously imaged in sharp focus (S310, "NO"), then the points Q1, Q2 and Q3 are jointly brought into focus again by tilting again. As soon as all three points are focused (S310, "YES"), that is the focal positions in the Z direction of the points Q1, Q2 and Q3 are identical, one of these values is used for calculating the lowering distance $Z_A$. After completing this procedure, the opening (tip) of the capillary 4 is parallel to the surface of the cell material 7 and the slide 8.

Finally, if greater accuracy is necessary (S320), then the correction of the tilt angle 12 and of the axial rotation 11 can also be repeated with a larger magnification (S260-S310). On the other hand, for small operating magnifications up to at most 20× it is possible to carry out the calibration directly with the working objective. Therefore, no replacement of the objective is necessary.

The invention claimed is:

1. A method for the collision-free positioning of a micromanipulation tool relative to a sample carrier with the aid of a microscope, comprising the following steps:
   a) determining the focal position $Z_p$ of at least one point P on the surface of the sample carrier by focusing a microscope objective with a first numerical aperture $NA_1$ on the at least one point;
   b) positioning the micromanipulation tool on the optical axis of the microscope;
   c) determining the focal position $Z_M$ of the micromanipulation tool by focusing the microscope objective or a second microscope objective with a second numerical aperture $NA_2$ smaller than the first numerical aperture $NA_1$ onto the tip of the micromanipulation tool;
   d) calculating a lowering distance $Z_A(P)$ taking into account a predetermined tolerance profile $\Delta Z$ by the following equation:

$$Z_A(P) = Z_M - Z_P - \Delta Z$$

where $$\Delta Z = \Delta Z_M + \Delta Z_P$$

wherein $\Delta Z_M$ and $\Delta Z_p$ is a predetermined tolerance in the determination of the position of the manipulation tool and the sample carrier, respectively;
   e) positioning the micromanipulation tool at the point P by lowering by the lowering distance $Z_A(P)$.

2. The method according to claim 1, wherein before carrying out step e), the steps c) and d) are repeated with a respective further, i-th microscope objective (i>1 and i>2) with a respectively increasing numerical aperture ($NA_i > NA_{i-1}$).

3. The method according to claim 1, wherein the tolerance $\Delta Z_M$ of the manipulation tool and/or the tolerance $\Delta Z_p$ of the sample carrier is given by the depth of focus $d_{tief,i}$ of the respective i-th objective used to determine its position, according to the following equation:

$$\Delta Z_{M,P} = d_{tief,i} = \frac{\lambda \cdot n}{NA_i^2} + \frac{n}{M_i \cdot NA_i} \cdot e$$

$$i = 1, 2, \ldots$$

where $\lambda$ is the wavelength of the observation light, n is the refractive index of the medium between the microscope objective and sample carrier, $M_i$ is the magnification of the i-th objective, and e is the resolving power of a video camera used for the observation.

4. The method according to claim 1, wherein before step e), the steps a) to d) are carried out for a plurality of predetermined points $P_j$ (j=1, 2, . . . ) on the surface of the sample carrier, the corresponding lowering distance $Z_A(P_j)$ for each point $P_j$ is stored in a database, and step e) is carried out for each point $P_j$ taking into account the stored lowering distance $Z_A(P_j)$.

5. The method according to claim 1,
   wherein before step e), the steps a) to c) are carried out for three points $P_1$, $P_2$, $P_3$ on the surface of the sampler carrier that do not lie on a straight line, from whose determined focal positions $Z_{p1}, Z_{p2}, Z_{p3}$ an equation of a plane E(P) is calculated, and in step d) the lowering distance $Z_A(P_j)$ for an arbitrary point $P_j$ on the surface of the sample carrier is determined by the equation $$Z_A(P_j) = Z_M - E(P_j) - \Delta Z.$$

6. The method according to claim 1, wherein in step c) the position of the tip of the manipulation tool is determined as focal position $Z_M$.

7. The method according to claim 6, wherein in step c) a rotation angle and a tilt angle of the manipulation tool are compensated by carrying out the following steps:
   c1) determining the focal position $Z_{Q1}$ of a first point $Q_1$ on the tip of the manipulation tool by focusing on the point $Q_1$,
   c2) rotating the manipulation tool about its axis and readjusting the microscope objective in order to focus the point $Q_1$ until the focal position $Z_{Q1}$ of the point $Q_1$ and a focal position $Z_{Q2}$ of a second point $Q_2$ on the tip of the manipulation tool are identical,
   c3) determining the focal position $Z_{Q3}$ of a third point $Q_3$ on the tip of the manipulation tool by focusing on the point $Q_3$,
   c4) tilting the manipulation tool about an axis parallel to the plane of the sample carrier and readjusting the microscope objective in order to focus the point $Q_3$ until the focal positions $Z_{Q1}$, $Z_{Q2}$ and $Z_{Q3}$ are identical,
   c5) fixing the focal position of the manipulation tool $Z_A = Z_{Q1}$.

8. The method according to claim 1, wherein in step a) in addition the focal position $Z_{cap}$ of a point R on the surface of a receiving vessel is determined by focusing the first microscope objective onto the point R.

9. The method according to claim 1, wherein the point or points on the surface of the sample carrier and/or of the receiving vessel are approached by displacing it with the aid of a positioning table.

10. The method according to claim 1,
wherein the determination of the focal position is carried out with the aid of an optical distance measurement system.

* * * * *